(12) United States Patent
Chapman et al.

(10) Patent No.: US 7,805,190 B2
(45) Date of Patent: Sep. 28, 2010

(54) DEFIBRILLATORS CUSTOMIZED FOR ANTICIPATED PATIENTS

(75) Inventors: Fred William Chapman, Newcastle, WA (US); Richard C. Nova, Kirkland, WA (US); David Robert Hampton, Woodinville, WA (US); James M. Owen, Redmond, WA (US); Robert Niskanen, Shoreline, WA (US); John Carlton Daynes, Redmond, WA (US); Ronald Eugene Stickney, Edmonds, WA (US); René Ann Young Mitchell, Redmond, WA (US); Gregory T. Kavounas, Kirkland, WA (US)

(73) Assignee: Physio-Control, Inc., Redmond, WA (US)

(*) Notice: Subject to any disclaimer, the term of this patent is extended or adjusted under 35 U.S.C. 154(b) by 1176 days.

(21) Appl. No.: 10/810,045

(22) Filed: Mar. 26, 2004

(65) Prior Publication Data

US 2004/0249419 A1 Dec. 9, 2004

Related U.S. Application Data

(60) Provisional application No. 60/460,100, filed on Apr. 2, 2003.

(51) Int. Cl.
*A61N 1/02* (2006.01)
*A61N 1/39* (2006.01)

(52) U.S. Cl. .......................... 607/5; 607/59
(58) Field of Classification Search ................ 607/4–5, 607/59; 128/903
See application file for complete search history.

(56) References Cited

U.S. PATENT DOCUMENTS

| 4,118,946 | A | 10/1978 | Tubin |
| 4,292,973 | A | 10/1981 | Yamauchi et al. |
| 4,353,359 | A | 10/1982 | Milbauer |

(Continued)

FOREIGN PATENT DOCUMENTS

WO　　WO 99/44552 A1　　9/1999

(Continued)

OTHER PUBLICATIONS

Carmichael, Mary, "Medical Testing at Home," Newsweek, May 19, 2003, pp. 67-68.

(Continued)

*Primary Examiner*—Carl H Layno
*Assistant Examiner*—Jessica Sarcione
(74) *Attorney, Agent, or Firm*—Shumaker & Sieffert, P.A.

(57) ABSTRACT

An external defibrillator is customized for at least one person, i.e., an anticipated patient, through creation of a profile for the anticipated patient that allows the defibrillator and users of the defibrillator to provide customized treatment to the patient. The profile may include treatment parameters for the anticipated patient, such as defibrillation therapy parameters selected for the patient. The profile may also include a baseline recording of a physiological parameter of the patient, and medical history and personal information regarding the patient. In some embodiments, the external defibrillator stores a profile for each of one or more anticipated patients within a memory. In other embodiments, a profile for an anticipated patient is stored within a medium associated with that anticipated patient. The medium may, for example, be a removable medium for external defibrillators.

27 Claims, 7 Drawing Sheets

U.S. PATENT DOCUMENTS

| | | | |
|---|---|---|---|
| 4,619,265 A | | 10/1986 | Morgan et al. |
| 5,261,243 A | | 11/1993 | Dunsmore |
| 5,285,781 A | * | 2/1994 | Brodard ........................ 607/59 |
| 5,350,417 A | | 9/1994 | Augustine |
| 5,456,691 A | | 10/1995 | Snell |
| 5,474,574 A | | 12/1995 | Payne et al. |
| 5,486,204 A | | 1/1996 | Clifton |
| 5,521,812 A | | 5/1996 | Feder et al. |
| 5,571,142 A | | 11/1996 | Brown et al. |
| 5,662,690 A | | 9/1997 | Cole et al. |
| 5,724,025 A | | 3/1998 | Tavori |
| 5,836,993 A | * | 11/1998 | Cole ........................... 607/59 |
| 5,850,630 A | | 12/1998 | Wilson |
| 6,012,179 A | | 1/2000 | Garrett et al. |
| 6,091,989 A | | 7/2000 | Swerdlow et al. |
| 6,101,413 A | | 8/2000 | Olson et al. |
| 6,141,584 A | * | 10/2000 | Rockwell et al. ................ 607/5 |
| 6,148,233 A | | 11/2000 | Owen et al. |
| 6,209,144 B1 | | 4/2001 | Carter |
| 6,269,267 B1 | | 7/2001 | Bardy et al. |
| 6,277,143 B1 | | 8/2001 | Klatz et al. |
| 6,301,502 B1 | | 10/2001 | Owen et al. |
| 6,321,113 B1 | | 11/2001 | Parker et al. |
| 6,334,070 B1 | | 12/2001 | Nova et al. |
| 6,356,785 B1 | | 3/2002 | Snyder et al. |
| 6,370,428 B1 | | 4/2002 | Snyder et al. |
| 6,389,828 B1 | | 5/2002 | Thomas |
| 6,406,427 B1 | | 6/2002 | Williams et al. |
| 6,409,745 B1 | | 6/2002 | Ducharme et al. |
| 6,416,480 B1 | | 7/2002 | Nenov |
| 6,426,759 B1 | | 7/2002 | Ting et al. |
| 6,461,379 B1 | | 10/2002 | Carson et al. |
| 6,468,210 B1 | | 10/2002 | Iliff |
| 6,473,920 B2 | | 11/2002 | Augustine et al. |
| 6,475,143 B2 | | 11/2002 | Iliff |
| 6,497,358 B1 | | 12/2002 | Walsh |
| 6,524,241 B2 | | 2/2003 | Iliff |
| 6,527,713 B2 | | 3/2003 | Iliff |
| 6,569,093 B2 | | 5/2003 | Iliff |
| 6,581,400 B2 | | 6/2003 | Augustine et al. |
| 6,682,550 B2 | | 1/2004 | Clifton et al. |
| 6,697,671 B1 | | 2/2004 | Nova et al. |
| 6,813,517 B2 | | 11/2004 | Daynes et al. |
| 6,829,501 B2 | | 12/2004 | Nielsen et al. |
| 6,887,199 B2 | | 5/2005 | Bridger et al. |
| 2002/0004729 A1 | | 1/2002 | Zak et al. |
| 2002/0072785 A1 | | 6/2002 | Nelson et al. |
| 2002/0103508 A1 | | 8/2002 | Mathur |
| 2002/0138302 A1 | | 9/2002 | Bodnick |
| 2002/0143366 A1 | | 10/2002 | Herleikson |
| 2003/0088284 A1 | | 5/2003 | Daynes et al. |
| 2003/0195567 A1 | | 10/2003 | Jayne et al. |

FOREIGN PATENT DOCUMENTS

| | | |
|---|---|---|
| WO | WO 00/33236 A1 | 6/2000 |
| WO | WO 01/95977 A1 | 12/2001 |
| WO | WO 02/41231 A2 | 5/2002 |

OTHER PUBLICATIONS

U.S. Appl. No. 10/620,742, filed Jul. 16, 2003, titled "First Aid System."

PCT Written Opinion from corresponding PCT Application No. PCT/US2004/010265, mailed on Feb. 24, 2005 (5 pages).

Sophie Cluet and Claude Delobel, "A General Framework for the Optimization of Object-Oriented Queries," ACM SIGMOD Record vol. 21, Issue 2, pp. 383-392 (Jun. 1992).

International Preliminary Report on Patentability from corresponding PCT Application Serial No. PCT/US2004/010265, mailed Jun. 23, 2005 (7 pages).

Medusa Medical Technologies, Inc. home page, archive dated May 5, 2002, downloaded from http://web.archive.org/web/20020808172506/www.medusa.ca/aboutus.htm on Mar. 26, 2006 (2 pages).

Medusa Medical Technologies, Inc. SIREN product page, archive date May 5, 2002, downloaded from http://web.archive.org/web/20020905071213/www.medusa.ca/products.htm on Mar. 26, 2006 (4 pages).

HealthWare Solutions home page, archive dated Sep. 27, 2002, downloaded from "Internet Archive Way Back Machine," web.archive.org, on Mar. 26, 2006 (1 page).

HealthWare Solutions, "EMS Software that Works as Hard as You Do," archive dated Sep. 27, 2002, downloaded from "Internet Archive Way Back Machine," web.archive.org, on Mar. 26, 2006 (1 page).

HealthWare Solutions, "EMS Solution 2000 Administrator, Manager, Query and Desktop Manager," archive dated Sep. 27, 2002, downloaded from "Internet Archive Way Back Machine," web.archive.org, on Mar. 26, 2006 (1 page).

HealthWare Solutions, "EMS Solution 2000 Notes," archive dated Sep. 27, 2002, downloaded from "Internet Archive Way Back Machine," web.archive.org, on Mar. 26, 2006 (1 page).

HealthWare Solutions, "EMS Solution 2000 LifePak Module, NFIRS Interface, Billing Interfaces and State Interfaces," archive dated Sep. 27, 2002, downloaded from "Internet Archive Way Back Machine," web.archive.org, on Mar. 26, 2006 (1 page).

HealthWare Solutions, "EMS Solution 2000 New Products," archive dated Sep. 27, 2002, downloaded from "Internet Archive Way Back Machine," web.archive.org, on Mar. 26, 2006 (1 page).

* cited by examiner

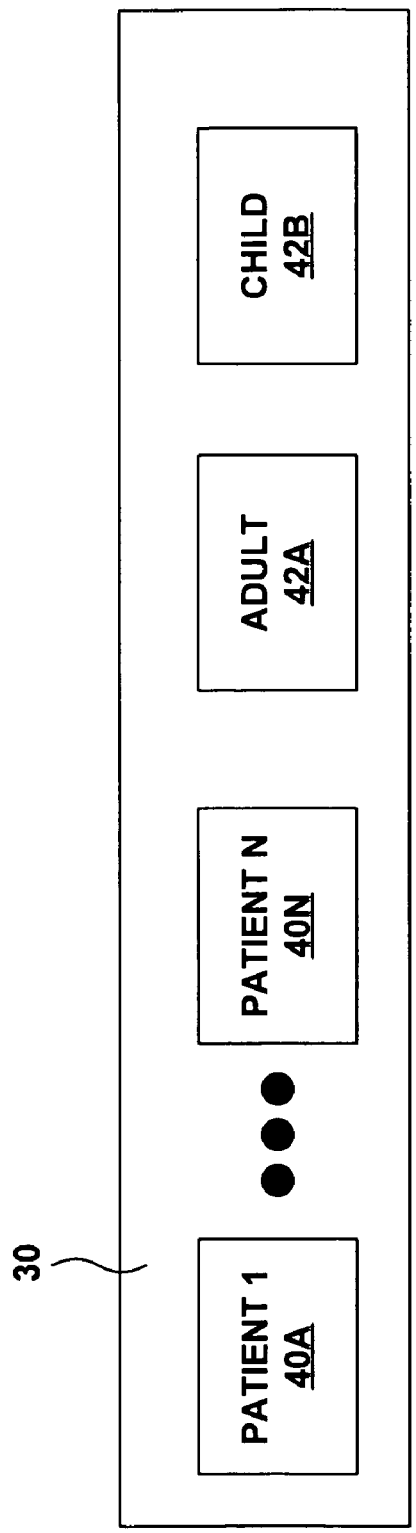

FIG. 3

PERSONAL INFORMATION: NAME/D.O.B./GENDER

CONSENT INFORMATION: CONSENT FOR CARE (E.G. "DO NOT RESUSCITATE")

CONTACT INFORMATION:
 NAMES/INFO OF: PHYSICIAN, HOSPITAL, INSURANCE

MEDICAL INFORMATION:
 HEIGHT, WEIGHT, MEDICATIONS, ALLERGIES, CHEST CIRCUMFERENECE, PRIOR CARDIAC CONDITIONS, IMPLANTED DEVICES, TRACKING INFORMATION FOR IMPLANTED DEVICES, NORMAL CARDIAC RHYTHM, STORED ECG WAVEFORMS, TRANSTHORACIC IMPEDANCE

THERAPY INFORMATION:
 THERAPY PARAMETERS

40

DEFIBRILLATORS CUSTOMIZED FOR ANTICIPATED PATIENTS

This application claims the benefit of U.S. Provisional Application Ser. No. 60/460,100, filed Apr. 2, 2003, the entire content of which is incorporated herein by reference.

TECHNICAL FIELD

The invention relates to medical devices, and more particularly, to external defibrillators.

BACKGROUND

Sudden cardiac arrest (SCA) can kill a victim. Also called sudden cardiac death, SCA is a condition in which the heart stops pumping enough blood to sustain vital organs. SCA is usually caused by life-threatening arrhythmias, which are abnormalities in the heart's electrical system. The most common arrhythmia at the onset of SCA is ventricular fibrillation (VF). In this condition, the heart's muscle cells contract too chaotically to be effective in pumping blood to the brain and other vital organs. A SCA event is different than a heart attack, e.g., acute myocardial infarction (AMI), although a person suffering from a heart attack is more likely to develop abnormal heart rhythms and SCA.

SCA is one of the leading causes of death among adults worldwide: it kills approximately 225,000 people a year in the United States. SCA is largely unpredictable, with two out of every three deaths occurring outside of the hospital. Although existing heart disease is a common cause of SCA, many victims have never experienced any prior heart problems. Further, although risk of SCA increases with age, SCA can happen to anyone—even a child.

Treatment for SCA must be administered as soon as possible to increase chances of survival. In the initial few minutes of the SCA event, the probability of survival diminishes by approximately 10% each minute. Emergency medical services (EMS) personnel may not arrive quickly enough to administer effective treatment. This problem is worsened in remote or sparsely inhabited areas that delay response times. Every minute of delay diminishes the probability of saving a life.

Responding to a SCA event typically requires special equipment. The most critical equipment is a defibrillator, which applies an electrical shock that stops the fibrillation, resynchronizes cardiac activity, and restores a perfusing rhythm. In many instances the first defibrillator to reach the victim is an automated external defibrillator (AED). AEDs are sometimes made available for public use in places where many people congregate or are hard to reach by EMS personnel (for example, inside an airplane). People who work in such places that deploy AEDs usually receive training for operating the AED. In addition, people are starting to purchase AEDs for their homes. The person that could be resuscitated may be the person that bought the defibrillator, someone from his or her immediate family, or a guest in their home.

Existing AEDs are given a general configuration, e.g., programmed with settings such that they are suitable for use to treat any victim within the public at large. When an existing AED is applied to a victim, there are no data regarding the victim's normal cardiac rhythm. Further, the victim may be unconscious, so there is no way to know from the victim information about their medical history, emergency contact information, and the like.

Because existing AEDs are configured generally, they may perform less than optimally for particular victims in the public at large. For example, a particular victim may naturally have a fast and/or irregular cardiac rhythm, e.g., via conduction of paroxysmal atrial fibrillation. In this case, the defibrillator may misdiagnose the rhythm as requiring defibrillation therapy, and may control or recommend delivery of defibrillation therapy.

SUMMARY

Generally, the present invention provides external defibrillators that are customized for at least one person, i.e., an anticipated patient. In particular, a profile is created for the anticipated patient that allows a defibrillator and users of the defibrillator to provide customized treatment to the patient. Customized treatment according to such a profile may be more effective in that it considers the unique physiological condition and the medical history of the anticipated patient. An anticipated patient may be a patient who is at elevated risk for sudden cardiac arrest (SCA).

The profile may include treatment parameters for the anticipated patient, such as defibrillation therapy parameters selected for the patient. The profile may also include a baseline recording of a physiological parameter of the patient, and medical history and personal information regarding the patient. A defibrillator or user of the defibrillator may use the recorded physiological parameter, medical history information, and personal information to determine whether treatment is appropriate for the anticipated patient, and what treatment is appropriate for the anticipated patient. The personal information may also be used to identify the patient. The profile may be updated periodically and/or based on treatment of the patient.

In some embodiments, the external defibrillator stores a profile for each of one or more anticipated patients within a memory. The defibrillator receives an indication of whether a patient to be treated is an anticipated patient and, if the defibrillator stores multiple profiles for multiple anticipated patients, receives an indication of the identity of the patient. For example, the defibrillator may provide a user interface that allows a user to select the patient which is to be treated so that the appropriate profile may be accessed. In other embodiments, the anticipated patient may carry a patient identification device, such as a radio-frequency identification (RFID) card, and the defibrillator may read the RFID card to determine which profile to access for patient. In still other embodiments the defibrillator may read biometric information of the patient, such as a fingerprint, to identify the patient.

In some embodiments, a profile for an anticipated patient is stored within a medium associated with that anticipated patient. The medium may, for example, be a removable medium for external defibrillators, e.g., a memory stick, or may be a medium within any device capable of being coupled to a defibrillator via a wired or wireless connection. The anticipated patient may keep the medium with them for use in the event that they need to be treated by an external defibrillator, and any external defibrillator capable of accessing the profile stored within the medium may use the profile to control treatment of the anticipated patient. For example, a user of an external defibrillator capable of accessing such media may retrieve the medium or device from the anticipated patient to facilitate customized treatment of the anticipated patient according to the profile.

In addition to storing or being capable of accessing a profile for an anticipated patient, an external defibrillator according to the invention stores or is otherwise capable of accessing at least one general profile for use in treating non-anticipated patient, e.g., patients within the general public. The general profile includes therapy parameters, e.g., defibrillation therapy parameters, suitable for members of the general public. In some embodiments, an external defibrillator stores or is otherwise capable of accessing a plurality of general profiles that are selectable. For example, in some embodiments, a defibrillator stores or can access an adult profile including defibrillation parameters, e.g., energy levels, suitable for adults, and a child profile including defibrillator parameters suitable for children.

In one embodiment, the invention is directed to a method in which it is determined whether a patient is an anticipated patient, and therapy is delivered to the patient according to one of a general profile and another profile associated with the anticipated patient based on the determination.

In another embodiment, the invention is directed to an external defibrillator comprising a therapy delivery module and a processor. The processor determines whether a patient is an anticipated patient, and controls delivery of therapy to the patient by the therapy delivery module according to one of a general profile and another profile associated with the anticipated patient based on the determination.

In another embodiment, the invention is directed to a computer-readable medium comprising instructions. When executed by a programmable processor, the instructions cause the programmable processor to determine whether a patient is an anticipated patient, and control delivery of therapy to the patient via an external defibrillator according to one of a general profile and another profile associated with the anticipated patient based on the determination.

In another embodiment, the invention is directed to a computer-readable medium comprising a profile for a patient. The profile is retrievable by an external defibrillator for delivery of therapy to the patient according to the profile, and includes at least one of medical history information for the patient, a previously recorded physiological parameter of the patient, and defibrillation therapy parameters.

In another embodiment, the invention is directed to a method in which information is collected relating to a patient. The information is stored as a profile for the patient that is retrievable by an external defibrillator for delivery of therapy according to the profile.

The invention can provide one or more advantages, including facilitating customized and potentially more efficacious treatment of one or more anticipated patients. In some cases, use of a profile for an anticipated patient may reduce the risk of misdiagnosis of the patient through consideration of baseline recordings of physiological parameters and the medical history of the patient. For example, a person with a naturally slow, fast, or irregular heart rhythm who may be misdiagnosed as requiring pacing or defibrillation by conventional external defibrillators, may be correctly diagnosed by comparison of a current ECG to a stored baseline ECG. Other conditions of a patient that may lead to misdiagnosis as requiring defibrillation, cardioversion or pacing therapies include electrocardiogram (ECG) abnormalities, e.g., prior myocardial infraction, bundle branch block, third degree atrioventricular dissociation, atrial fibrillation, frequent premature ventricular complexes, long QT syndrome, ventricular hypertrophy, and the like.

Embodiments in which a profile for an anticipated patient is stored on a medium associated with the anticipated patient may allow the patient to receive customized treatment in a variety of situations and locations, e.g., wherever an external defibrillator capable of accessing the medium is available. On the other hand, a defibrillator that stores one or more anticipated patient profiles may not be intended for public use, but may be procured primarily for a particular person or group of people, who may be at elevated risk for sudden cardiac arrest. A family thus can own a single defibrillator with anticipated patient profiles for each of the family members, and one or more general profiles that may be used for guests. As another example, a nursing home or other group care setting could own a defibrillator with anticipated patient profiles for a number of residents, and one or more general profiles that may be used for guests.

In some embodiments in which a defibrillator stores a profile for an anticipated patient, the defibrillator may be able to provide a number of features for the anticipated patient in addition to customized emergency medical treatment. For example, the profile may store information about treatments provided to the anticipated patient that can be retrieved by a medical practitioner or manufacturer of the defibrillator either during a scheduled visit, or via a network. As another example, the profile may provide customized first aid information to the anticipated patient. Further, the profile may store medication information or information about other regularly scheduled treatment events, and the defibrillator may provide reminders or other information to the patient to regarding the medication or other regularly scheduled treatment events.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 2 is a block diagram illustrating an example configuration of a memory of the external defibrillator of FIG. 1.

FIG. 3 is a conceptual diagram illustrating an example profile for an anticipated patient.

DETAILED DESCRIPTION

Figure 1:
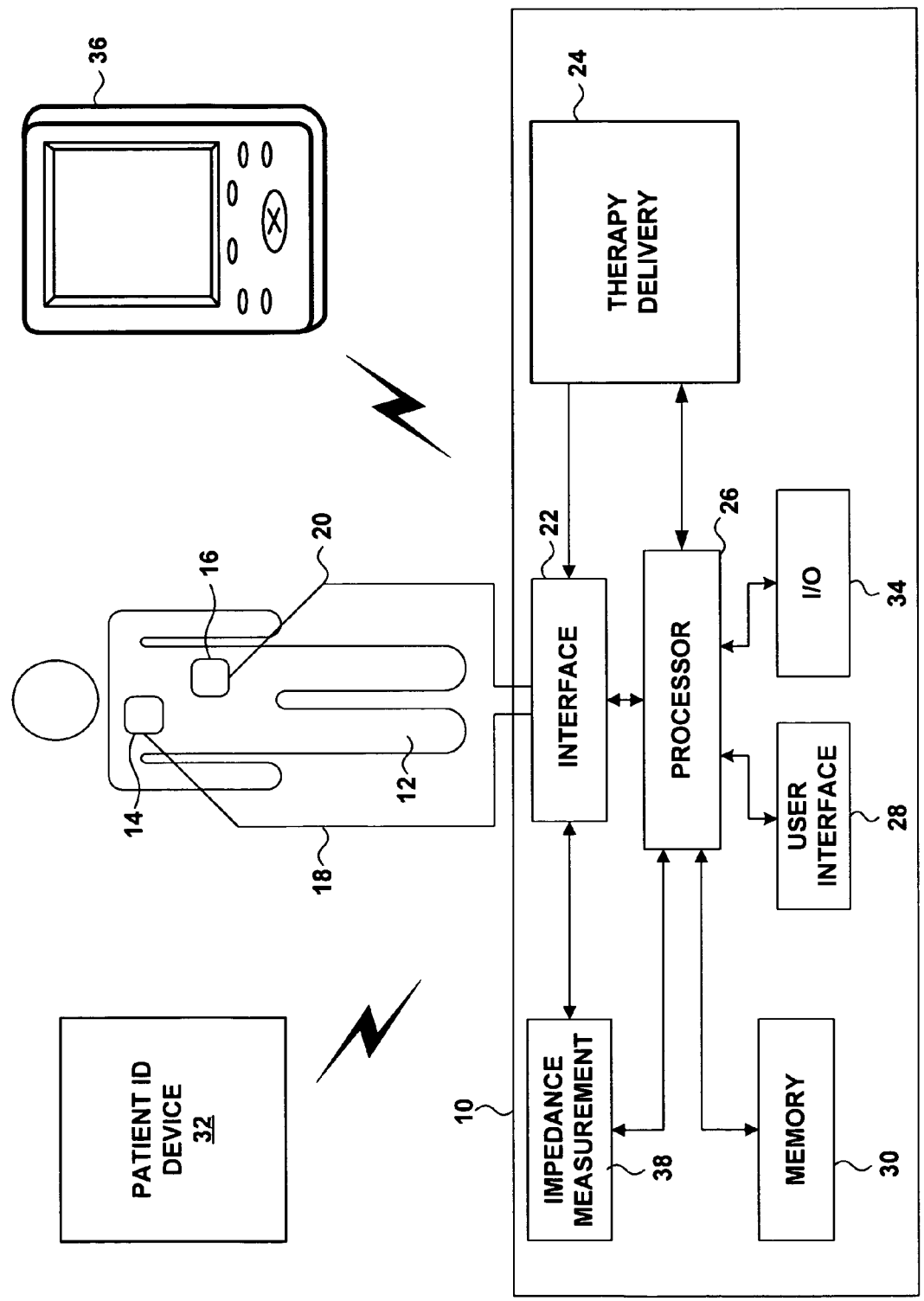
FIG. 1 is a block diagram of an example external defibrillator that stores a profile for an anticipated patient coupled to a patient in accordance with the invention.

FIG. 1 is a block diagram of an example external defibrillator 10 coupled to a patient 12. As will be described in greater detail below, defibrillator 10 is customized for an anticipated patient, e.g., a patient who is at elevated risk for sudden cardiac arrest (SCA). In particular, defibrillator 10 stores a profile for the anticipated patient within memory 30. The profile allows defibrillator 10 and users of defibrillator 10 to provide customized treatment the anticipated patient. Customized treatment according to such a profile may be more effective in that it considers the unique physiological condition and the medical history of the anticipated patient.

Defibrillator 10 is capable of delivering therapy, such as defibrillation, cardioversion, or pacing pulses, to patient 12 via electrodes 14 and 16, which may be hand-held electrode paddles or adhesive electrode pads placed on the skin of patient 12. The body of patient 12 provides an electrical path between electrodes 14 and 16. Electrodes 14 and 16 are coupled to defibrillator 10 via conductors 18 and 20 and interface 22. In a typical application, interface 22 includes a receptacle, and conductors 18 and 20 plug into the receptacle.

Defibrillator 10 includes therapy delivery circuitry 24 for delivery of therapy to patient 12. Therapy delivery circuitry 24 may include well-known components, such as capacitors and switches, for storage of electrical energy and delivery of the electrical energy in the form of pulses to patient 12. Interface 22 may also include one or more switches to couple therapy delivery circuit 24 to electrodes 14 and 16.

A processor 26 interacts with one or both of therapy delivery circuitry 24 and interface 22 to control delivery of therapy to patient 12. For example, processor 26 may control delivery of defibrillation, cardioversion, or pacing pulses based on selected pulse characteristics, e.g., energy level, amplitude, width, shape, or rate. Processor 26 may take the form of a microprocessor, digital signal processor (DSP), application specific integrated circuit (ASIC), field-programmable gate array (FPGA), or other logic circuitry programmed or otherwise configured to operate as described herein.

Defibrillator 10 may be a manual or automated external defibrillator. For delivery of defibrillation therapy for example, where defibrillator 10 is a manual defibrillator, a user of defibrillator 10 may select at least one characteristic, e.g., energy level, for each defibrillation pulse delivered to patient 12. Processor 26 may receive the selection made by the user via a user interface 28, which may include input devices, such as a keypad, and output devices, such as various indicator lights, a CRT, LED, or LCD screen, and a speaker. Output devices included as part of user interface 28 may also include a printer, such as printer in the home of patient that is coupled to processor 26 via a wireless network connection. Where defibrillator 10 is an automated defibrillator, processor 26 may select the characteristics of the delivered therapy, e.g., may select energy levels for defibrillation pulses from a preprogrammed progression of energy levels stored in a memory 30 based on number of defibrillation pulses already delivered to patient 12.

Processor 26 may perform other functions as well, such as monitoring electrocardiogram (ECG) signals sensed via electrodes 14 and 16 and received via interface 22. Processor 26 may monitor the ECG to determine whether to deliver therapy to patient 12, determine what therapy to delivery to patient 12, and determine whether delivery of therapy has been effective or successful. For example, processor 26 may determine whether the heart of patient 12 is fibrillating based upon the ECG signals in order to determine whether a defibrillation pulse should be delivered to patient 12. Where a defibrillation pulse has already been delivered, processor 26 may evaluate the efficacy of the delivered defibrillation pulse by determining if the heart is still fibrillating in order to determine whether an additional defibrillation pulse is warranted. Processor 26 may automatically control delivery of therapy to patient 12 based on these determinations, or may advise the user of defibrillator 10 of these determinations via user interface 32.

Processor 26 controls delivery of therapy and/or provides information, such as treatment suggestions, to a user of defibrillator 10 according to one of a plurality of profiles stored in memory 30. In particular, memory 30 stores at least one profile for an anticipated patient, and at least one general profile for non-anticipated patients. An anticipated patient profile, as mentioned above, allows defibrillator 10 and users of defibrillator 10 to provide customized treatment the anticipated patient, while the one or more general profiles allow defibrillator 10 or users or defibrillator 10 to provide treatment suitable for the general patient in the event that defibrillator 10 is used to treat a non-anticipated patient.

A profile for an anticipated patient may include therapy parameters tailored for the anticipated patient, such as energy levels or other characteristics for one or more progressions of defibrillation pulses tailored to provide effective defibrillation of the anticipated patient. The energy levels for defibrillation pulses may be tailored based on the transthoracic impedance of the patient, or on other information about the anticipated patient such as information that the patient has been taking anti-arrhythmic medication or medication that alters the defibrillation threshold. The profile may also include a baseline recording of a physiological parameter of the anticipated patient, such as a baseline ECG recording.

As described above, processor 26 may monitor a current ECG of patient 12 when coupled to patient 12 to treat patient 12 in order to determine whether to deliver therapy to patient 12, determine what therapy to delivery to patient, and determine whether delivery of therapy has been effective or successful. If patient 12 is an anticipated patient and memory 30 stores an anticipated patient profile for patient 12 that includes a baseline ECG recording, processor 26 may compare the current ECG to the baseline ECG recording for these purposes, which may allow processor 26 to avoid misdiagnosing patient 12. For example, comparison of a currently recorded ECG and a baseline ECG recording may avoid misdiagnosis of patient 12 with electrocardiogram (ECG) abnormalities such as moderate sinus bradycardia, prior myocardial infarction, bundle branch block, third degree atrioventricular dissociation, moderate sinus bradycardia, atrial fibrillation, frequent premature ventricular complexes, long QT syndrome, ventricular hypertrophy, and the like as requiring defibrillation, cardioversion or pacing therapy.

An anticipated patient profile may also include medical history information and personal information regarding the patient. If patient 12 is an anticipated patient and memory 30 stores an anticipated patient profile for patient 12, processor 26 or a user of defibrillator 10 may also use medical history information and personal information to determine whether treatment is appropriate for the anticipated patient, and what treatment is appropriate for the anticipated patient. For example, the anticipated patient profile may indicate that patient 12 has an implantable pacemaker, cardioverter, and/or defibrillator. In such cases, processor 26 may determine or advise a user of defibrillator 10 that delivery of therapy to patient 12 via defibrillator 10 should be delayed to allow the implanted device to deliver therapy. The anticipated patient profile may include information about the type of device and its behavior, e.g. pace pulse characteristics such as defibrillation pulse amplitude, width, rate, duration, and timing. If the implanted device failed, which may occur due to a failure to detect VF, a depleted battery, or other cause, defibrillator 10 would be prepared to delivery therapy according to the profile. Processor 26 may also present the personal information to a user of defibrillator 10 via user interface 28 to allow the user to identify patient 12.

In some embodiments, I/O circuitry 34 and user interface 28 may include circuitry to allow a user of defibrillator 10 to communicate with a remote medical professional, e.g., a physician, while responding to a medical emergency involving patient 12. For example, I/O circuitry 34 may comprise a cellular telephone transceiver, and user interface 28 may comprise a speaker and a microphone. The user of defibrillator 10 may verbally provide information regarding the condition of patient 12 to the medical professional, and may receive instruction as to how to treat patient 12 from the medical professional. In some embodiments, processor 26 may also transmit information to the medical professional via the communication channel, such as an ECG of patient 12, which may be displayed to the medical professional via a computer or workstation. In embodiments in which patient 12 is an anticipated patient, processor 26 may also transmit at least some of the anticipated patient profile associated with patient 12, such as medical history information and a baseline ECG sample, which may be displayed to the medical professional via the computer or workstation. The medical professional may advise the user of defibrillator 10 as to how to treat patient 12 based on the anticipated patient profile information.

Memory 30 also stores at least one general profile that is used to treat non-anticipated patients. The general profile may include therapy parameters, e.g., progressions of pulse energy levels, suitable for an average patient in the public at large. If processor 26 determines that patient 12 is not an anticipated patient, processor 26 controls delivery of therapy to patient 12 according to a general profile When defibrillator 10 is activated to treat patient 12, processor 26 determines whether patient 12 is an anticipated patient. In particular, processor 26 may receive an indication of whether patient 12 is an anticipated patient and, if memory 30 stores multiple anticipated patient profiles, receives an indication of the identity of patient 12 for use in selecting the appropriate one of the anticipated patient profiles. For example, a user of defibrillator 10 may provide these indications to processor 26 via user interface 28.

In other embodiments, patient 12 (if an anticipated patient) may carry a patient identification device 32, such as a radio-frequency identification (RFID) card or an identification card including a readable magnetic stripe, and processor 26 may read identification device 32 to determine which profile to access for patient 12. In such embodiments, input/output circuitry 34 may comprise a card-reader or the like to enable identification of patient 12. In still other embodiments, input/output circuitry 34 may include a scanner to read biometric information of patient 12, such as a fingerprint, in order to identify patient 12.

In addition to the above-described therapy mode in which processor 26 controls delivery of therapy to patient 12 based on a selected profile, processor 26 may also provide a programming mode in which an anticipated patient profile is created for patient 12. After purchase or prescription of defibrillator 10 for patient 12, for example, a clinician or patient 12 may direct processor 26 to enter the programming mode so that an anticipated patient profile may be created for patient 12. The clinician or patient 12 may interact with processor 26 to create the profile for patient 12 via one or both of user interface 28 or a programming device 36.

Programming device 36 is a computing device and may, as shown in FIG. 1, take the form of a handheld computer. In embodiments of defibrillator 10 in which programming device 36 is used to create anticipated patient profiles, input/output circuitry 34 may include circuitry for wired or wireless communication with programming device 36. Wireless communication between programming device 36 and defibrillator 10 may be according to any of a variety of local wireless communication techniques, such as RF communication according to the 802.11 or Bluetooth specification sets, infrared communication according to the IRDA specification set, or other standard or proprietary wireless communication protocols. In some embodiments, input/output circuitry 34 may include network interface circuitry, and defibrillator 10 may communicate with programming device 36 via a network such as the Internet.

The clinician or patient 12 may enter personal information and medical history information for creation of the anticipated patient profile stored in memory 30 in response to structured queries provided by defibrillator 10 or programming device 36, or the information may be extracted from, for example, patient files capable of being accessed by programming device 36 or defibrillator 10. With defibrillator 10 coupled to patient 12, processor 26 may record a physiological parameter, e.g., make a baseline ECG recording, for inclusion in the anticipated patient profile. Further, processor 26 may direct impedance measurement circuitry to measure the transthoracic impedance of patient 12 via any of a variety of known impedance measurement techniques for use in determining a defibrillation pulse energy levels tailored for patient 12, which are then included within the anticipated patient profile for patient 12 within memory 30. Processor 26 may record the physiological parameter and control impedance measurement in response to a command from a clinician, or automatically upon entry into the programming mode or detecting that electrodes 14 and 16 have been coupled to patient 12. Further, a biometric reading may be collected by defibrillator 10 for inclusion in the profile in embodiments in which biometric measurements are used to identify anticipated patients.

The anticipated patient profile may be updated, e.g., periodically and/or in response to events. For example, the profile may automatically updated in response to treatment of patient 12, e.g., to indicate that patient 12 was treated and the condition of patient 12 that lead to treatment. As another example, the information, and particularly the physiological parameter recording, included as part of the anticipated patient profile may be periodically updated so that it is current. In some cases, the physiological parameter recording or therapy parameters of the anticipated patient profile may be updated in response to a newly identified or changed medical condition of patient 12 and/or new medication or change to a medication taken by patient 12, which may affect the efficacy of the previous therapy parameters or, for example, the patient's baseline ECG.

In addition to anticipated patient profiles and general profiles, memory 30 may include program instructions that cause processor 26 to perform the functions ascribed to processor 26 herein, as describe herein. Memory 30 may include any of a variety of volatile, non-volatile, fixed, removable, magnetic, optical, or electrical media, such as a random access memory (RAM), read-only memory (ROM), CD-ROM, hard disk, removable magnetic disk, memory cards or sticks, non-volatile RAM (NVRAM), electronically-erasable programmable ROM (EEPROM), flash memory, and the like.

FIG. 2 is a block diagram illustrating an example configuration of memory 30 of external defibrillator 10. As illustrated in FIG. 2, memory 30 stores a plurality of anticipated patient profiles 40A-40N for a plurality of anticipated patients, e.g., an anticipated patient profile for each member of a household or each of a plurality of group home residents. Further, in the illustrated embodiment, memory 30 stores two general profiles, an adult profile 42A and a child profile 42B. Adult profile 42A may include therapy parameters suitable for an average adult in the general population, e.g., defibrillation pulse energy levels which are suitable for defibrillation of such an adult. Child profile 42B may include therapy parameters for suitable for an average child in the general population, e.g., defibrillation pulse energy levels that are lower than adult levels and are therefore suitable for defibrillation of such a child.

If, when coupled to patient 12, processor 26 (FIG. 1) either receives an indication that patient 12 is not an anticipated patient or does not receive an indication that patient 12 is an anticipated patient, processor 26 may then determine whether patient 12 is an adult or a child in order to select the correct one of general profiles 42A and 42B for treatment of patient 12. Processor 26 may receive an indication of the age-related classification of patient 12 in a number of ways. For example, the user of defibrillator 10 may determine whether patient 12 is an adult or a child, and processor 26 may receive an input from the operator indicating the classification via user interface 28.

As another example, processor 26 may detect a type of electrodes 14 and 16 via interface 22, and determine the classification of patient 12 based on the electrode type. Different types of electrodes 14 and 16 may be used by the operator depending on whether patient 12 is an adult or a child. Connectors (not shown) between conductors 18 and 20 and interface 22 may include circuits with a particular resistance that indicates whether electrodes 14 and 16 are for use with adults or children. Processor 26 may direct interface 22 to apply a constant voltage or current to the circuits, and detect the electrode type based on a resulting current or voltage measured by interface 22.

Although described herein in the context of two general profiles, i.e., adult and child, the invention is not so limited. A memory 30 of a defibrillator 10 according to the invention may store any number of general profiles that are selectable based on one or more characteristics of a class of patients. For example, in some embodiments a memory 30 may store an adolescent profile in addition to the adult and child profiles 42A and 42B.

FIG. 3 is a conceptual diagram illustrating an example anticipated patient profile 40. As shown in FIG. 3, the anticipated patient profile may include personal information useful for identifying the patient prior to or after treatment, and contact information useful in determining how to handle or bill the patient after treatment with defibrillator 10. For example, in some embodiments, the contact information may include emergency contact information, e.g., telephone numbers to call in the event that there is a medical emergency involving patient 12, such as a number to reach a family member or a physician. Defibrillator 10 may present the emergency contact information to a user via user interface 28 upon identifying patient 12. In some embodiments, profile 40 may include a "do not resuscitate" (DNR) order that may be used by processor 26 or a user of defibrillator 10 to determine whether delivery of therapy to patient 12 is appropriate. For example, in some embodiments, defibrillator 10 may provide an indication to a user that patient 12 is not to be defibrillated via user interface 28 based on a DNR order within profile 40.

Profile 40 may also include medical information, such as height, weight, chest circumference, prior heart problems, presence of an implanted medical device, location of the implanted medical device, information about any medications, and the like, which may be used by processor 26 and/or a user of defibrillator 10 as described above. Further, profile 40 may include a recorded physiological parameter, e.g., an ECG recording, and therapy parameters, as described above.

In some embodiments, the patient history information stored by profile 40 may include information that could be used by a user of defibrillator 10 to provide first aid treatment to patient 12 whether or not patient 12 is in cardiac arrest. For example, defibrillator 10 may present the information stored in profile to the user via user interface 28 to assist the user in determining why patient 12 is unconscious or displaying other symptoms. The patient history information included within patient profile 40 may include, for example, information indicating that patient 12 is diabetic, has a family history or previous history of abdominal or thoracic aortic aneurysm, has a family history or previous history of stroke, or the like. Patient profile 40 may also include information instructing the user regarding a proper course of treatment for such conditions, and defibrillator 10 may present the treatment information via user interface 28.

Figure 4:
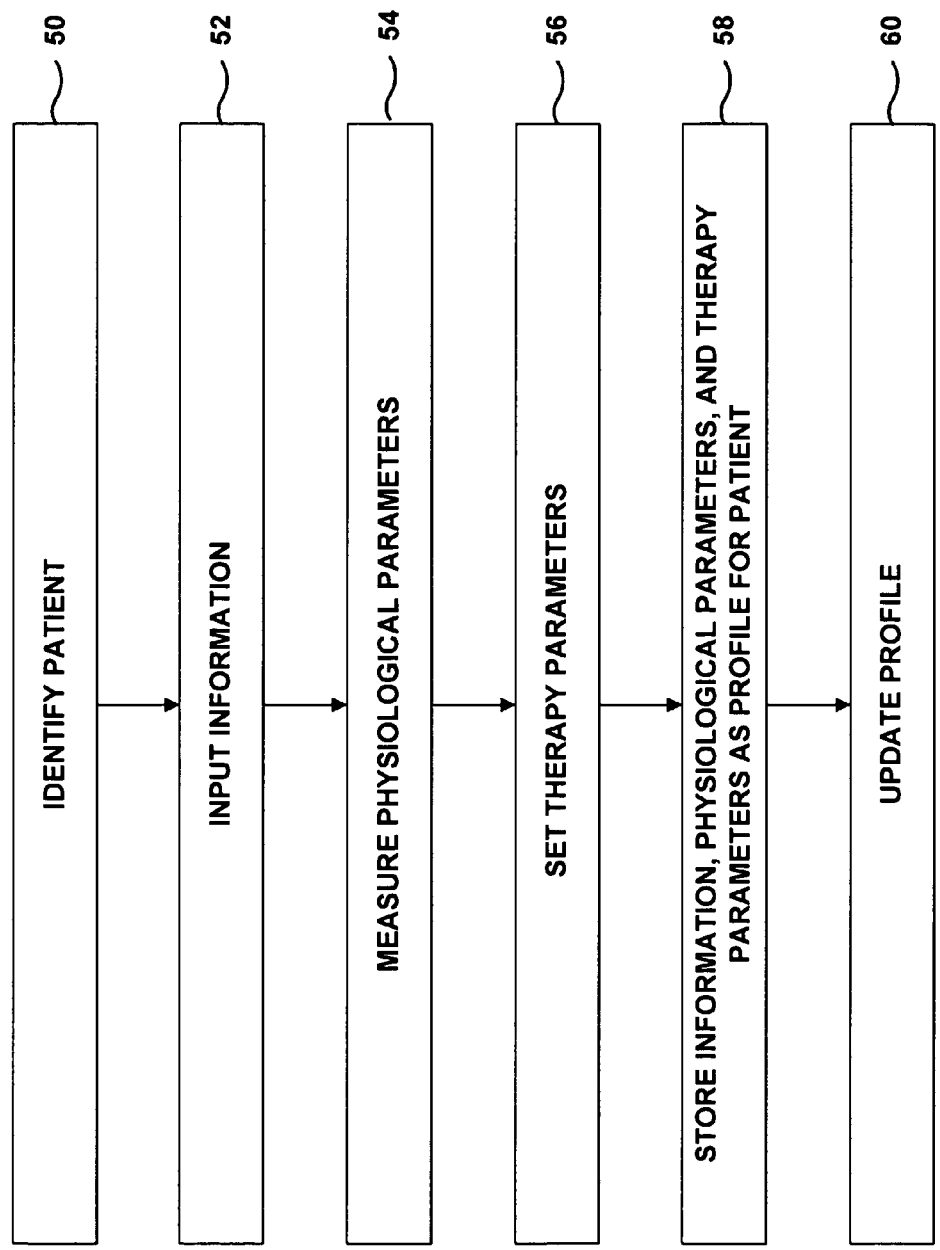
FIG. 4 is a flow diagram illustrating creation of a profile for an anticipated patient.

FIG. 4 is a flow diagram illustrating creation of an anticipated patient profile 40 for patient 12. Patient 12 is identified (50). In other words, identification and, in some cases, biometric information is collected from patient 12 via programming device 36 or user interface 28. Medical history information, and other information such as DNR order are input with the identification information via programming device 36 or user interface 28 (52). With defibrillator 10 coupled to patient 12, one or more physiological parameters of patient 12 may be measured for a baseline recording, e.g., a baseline ECG recording may be made (54). Further, therapy parameters tailored for patient 12 may be determined, e.g., via impedance measurement, as described above (56). The information, physiological parameter recording, and therapy parameters are stored within memory 30 as part of a patient profile 40. The profile 40 may be periodically updated, e.g., at clinic visits, and/or may be updated upon treatment of patient 12 (60).

Figure 5:
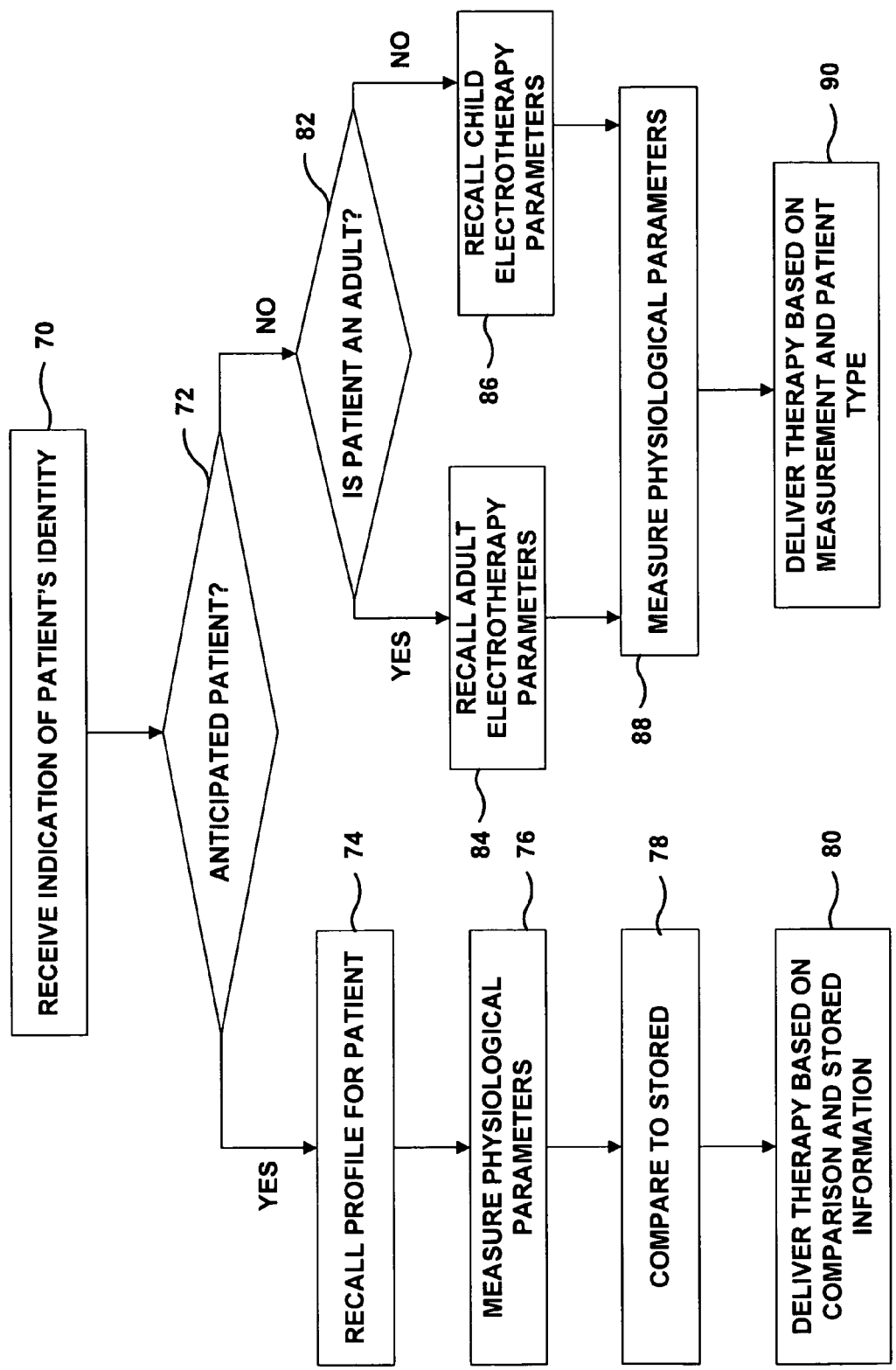
FIG. 5 is a flow diagram illustrating an example method that may be employed by an external defibrillator to diagnose and treat a patient.

FIG. 5 is a flow diagram illustrating an example method that may be employed by external defibrillator 10 to diagnose and treat a patient based on an anticipated patient profile 40. Processor 26 of defibrillator 10 receives an indication of an identity of patient 12 (70), and determines whether patient 12 is an anticipated patient (72). For example, processor 26 may receive an indication as to whether patient 12 is an anticipated patient or general patient via user interface 28, or by detecting a patient identification device 32. Where profiles 40 are stored for multiple anticipated patients within memory 30, processor 26 may also receive an indication of the identity of patient 12 via user interface 28 or the identification device 32 so that the correct profile 40 may be selected for patient 12.

If patient 12 is an anticipated patient, processor 26 accesses the correct anticipated patient profile 40 for patient 12 (74). Processor 26 may then take a current measurement of a physiological parameter of patient, such as a current recording of an ECG (76), and compare the current value to a stored value in order to determine whether delivery of therapy to patient is appropriate and what therapy is appropriate for patient 12 (78). Processor 26 controls or recommends delivery of therapy based on the comparison and any therapy parameters stored in the selected profile 40 (80).

If patient 12 is not an anticipated patient, but is instead a general patient, processor 26 determines whether patient 12 is an adult or a child according to any of the techniques described above (82). Based on the determination, processor 26 accesses one of adult profile 42A and child profile 42B (84, 86), which may include therapy parameters. Processor measures physiological parameters, and recommends or controls delivery of therapy based on the information within the selected one or profiles 42 (88, 90).

As described above, in some embodiments, a user of defibrillator 10 may verbally provide information regarding the condition of patient 12 to a remote medical professional via a communication channel provided by defibrillator 10, and may receive instruction as to how to treat patient 12 from the medical professional via the communication channel. In some embodiments, defibrillator 10 may also transmit information to the medical professional via the communication channel, such as an ECG of patient 12, which may be displayed to the medical professional via a computer or workstation. In embodiments in which patient 12 is an anticipated patient, defibrillator 10 may also transmit at least some of the anticipated patient profile associated with patient 12, such as medical history information and a baseline ECG sample, which may be displayed to the medical professional via the computer or workstation. The medical professional may advise the user of defibrillator 10 as to how to treat patient 12 based on the anticipated patient profile information.

Figure 6:
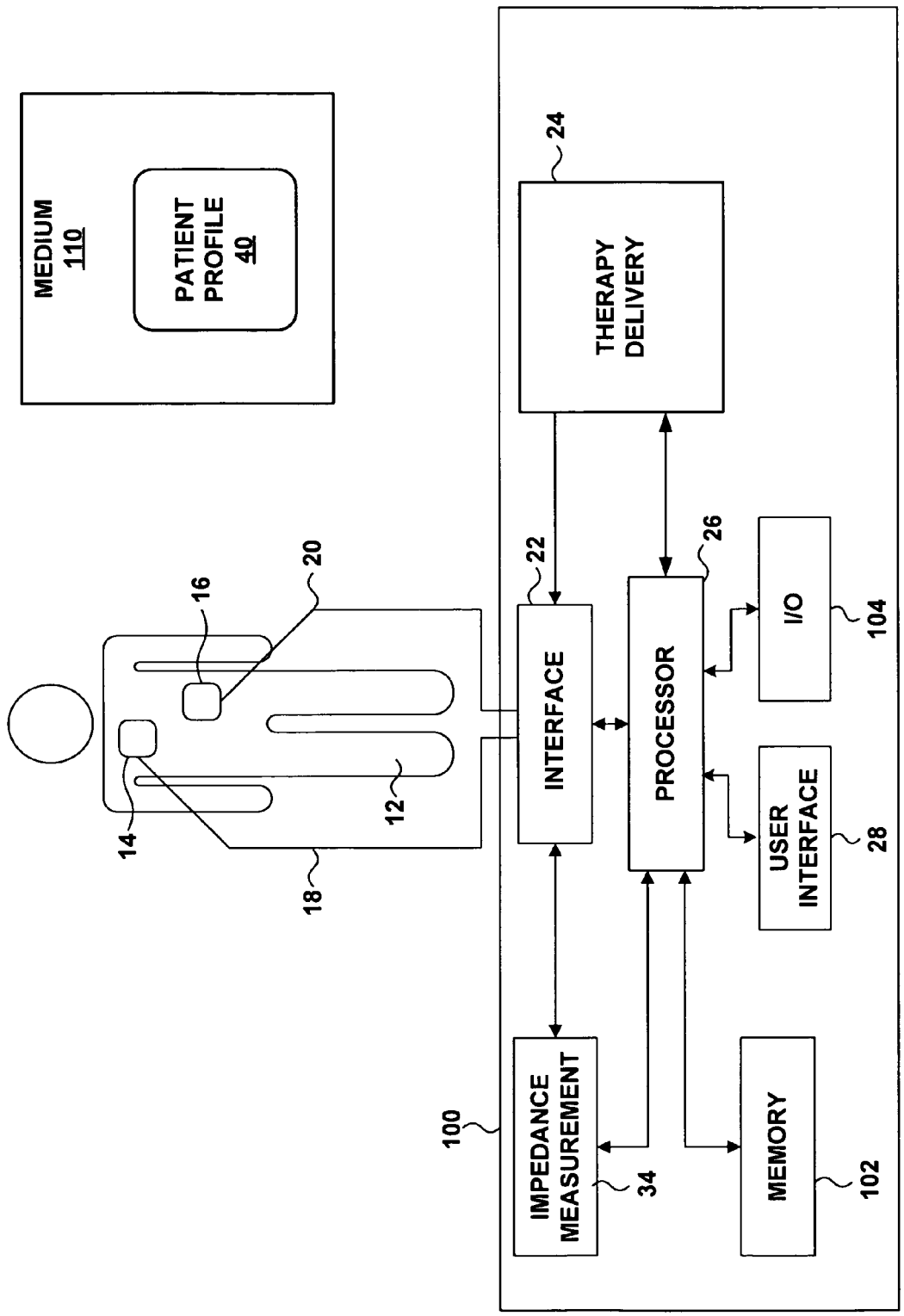
FIG. 6 is a block diagram illustrating another example external defibrillator coupled to a patient and a medium that stores profile for an anticipated patient.

FIG. 6 is a block diagram illustrating another example external defibrillator 100 coupled to patient 12 and a medium 110 that stores an anticipated patient profile 40 for patient 12. Medium 110 is associated with that anticipated patient. Medium 110 may, for example, be a removable medium for external defibrillators, e.g., a memory stick or card.

In other embodiments, medium 110 may be an RFID device that both identifies patient 12 and stores an anticipated patient profile for patient 12. Defibrillator 100 may interrogate the RFID device to identify patient 12 and receive the profile. In still other embodiments, medium 110 may be a medium within any device that is associated with patient 12 and capable of being coupled to a defibrillator via a wired or wireless connection, such as a cellular phone or personal digital assistant (PDA). In still other embodiments, the medium may be remotely located from patient, e.g., within a database maintained by a central EMS, pharmacy, hospital, clinic, or manufacturer of defibrillator 100, that defibrillator 100 may access via a network e.g., via a local-area network (LAN) cellular telephone network, public-switched telephone network, and/or the Internet.

In such embodiments in which a medium 110 associated with patient 12 stores the anticipated patient profile, defibrillator 100 may be a "public" defibrillator, e.g., not associated with patient 12 or particular group setting. Further, memory 102 of defibrillator 100 may store only one or more general profiles for treatment of patients in the general public. However, defibrillator 100 includes input/output circuitry 104 that includes circuitry for accessing anticipated patient profiles 40 stored within media 110, e.g., a memory stick reader, universal serial bus (USB) port, or wired or wireless networking interface. Processor 26 may access such media 110 to enable customized treatment of anticipated patients according to their anticipated patient profiles. Patient 12, for example, may keep medium 110 including his or her profile 40 on his or her person for use in the event that they need to be treated by an external defibrillator. The profile 40 may be created in any of the ways described above, including use of a defibrillator or other monitoring device and a programming device.

Figure 7:
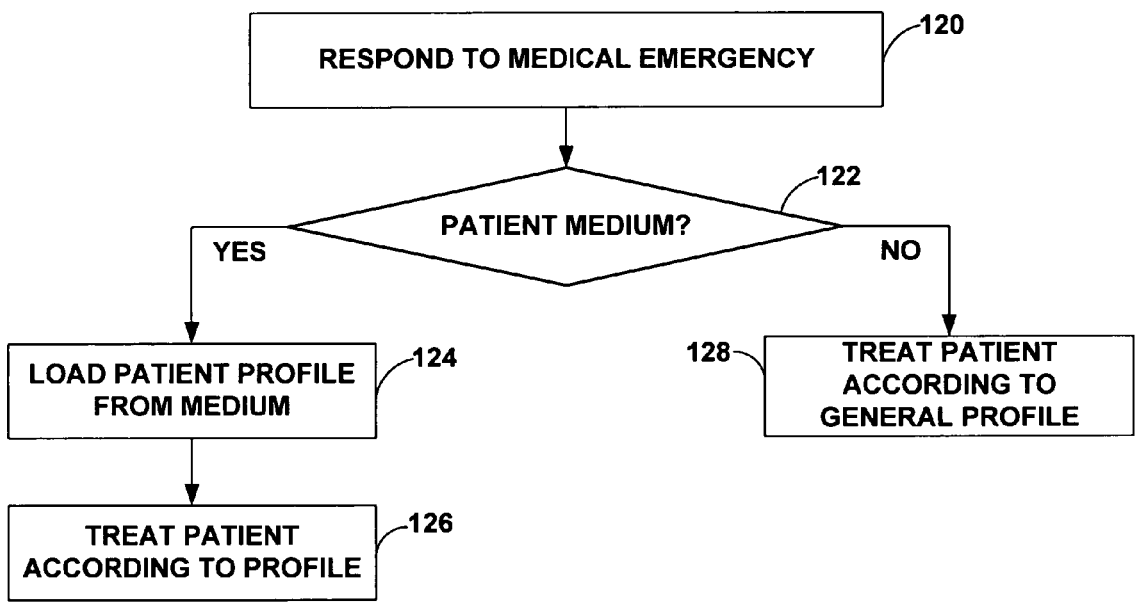
FIG. 7 is a flow diagram illustrating another example method that may be employed by an external defibrillator to diagnose and treat a patient.

FIG. 7 is a flow diagram illustrating another example method that may be employed by external defibrillator 100 to diagnose and treat patient 12. Defibrillator 100 is activated to respond to a medical emergency (120), and processor 26 determines whether a patient medium 110 is available to access (122). If a patient medium 110 is detected, processor 40 loads or accesses the patient profile 40 from the medium 110, and controls delivery of or recommends treatment according to the profile 40 (124, 126). If no patient medium 110 is detected, the patient 12 is treated according to a general profile 42 stored in a memory 102 of defibrillator 100 (128). Defibrillator 100 may also provide a communication channel with a remote medical professional, and may provide current patient condition information and at least some information stored in an anticipated patient profile to the remote medical professional, as described above with reference to defibrillator 10.

Various embodiments of the invention have been described. However, one skilled in the art will appreciate that various modifications may be made to the described embodiments without departing from the scope of the invention. For example, in some embodiments in which a defibrillator stores a profile for an anticipated patient, the defibrillator may be able to provide a number of features for the anticipated patient in addition to customized emergency medical treatment.

For example, the profile may store information about treatments provided to the anticipated patient that can be retrieved by a medical practitioner or manufacturer of the defibrillator either during a scheduled visit, or via a network. As another example, the profile may provide customized first aid information to the anticipated patient. Further, the profile may store medication information or information about other regularly scheduled treatment events, and the defibrillator may provide reminders or other information to the patient to regarding the medication or other regularly scheduled treatment events.

As another example, although general profiles have been described herein as stored within a memory of an external defibrillator, the invention is not so limited. General profiles may be stored within a memory of an external defibrillator, a removable medium for an external defibrillator, or any memory that may be accessed by an external defibrillator, e.g., via a wired, wireless, and/or network connection. Similarly, anticipated patient profiles may stored within a memory of an external defibrillator, a removable medium for an external defibrillator, or any memory that may be accessed by an external defibrillator, e.g., via a wired, wireless, and/or network connection. These and other embodiments are within the scope of the following claims.

The invention claimed is:

1. An external defibrillator comprising:
a therapy delivery module; and
a processor to determine whether a patient is one of an anticipated patient or a non-anticipated patient, wherein the anticipated patient is an individual patient associated with a patient-specific, customized profile, and to control delivery of therapy to the patient by the therapy delivery module according to one of a general profile if the patient is the non-anticipated patient or the customized profile if the patient is the anticipated patient.

2. The external defibrillator of claim 1, further comprising a user interface, wherein the processor receives an indication from a user via the user interface, and determines whether the patient is the anticipated patient based on the indication.

3. The external defibrillator of claim 1, further comprising an input circuit, wherein the processor receives an indication from a patient identification device associated with the anticipated patient via the input circuit, and determines whether the patient is the anticipated patient based on the indication.

4. The external defibrillator of claim 3, wherein the patient identification device comprises a radio-frequency identification (RFID) device.

5. The external defibrillator of claim 1,
further comprising at least one of a user interface and an input circuit,
wherein the processor receives information identifying the patient via at least one of the user interface and the input circuit, selects one of a plurality of patient-specific, customized profiles based on the identification, each of the customized profiles associated with a respective one of a plurality of anticipated patients, and controls delivery of therapy according to the selected customized profile.

6. The external defibrillator of claim 1,
further comprising an input circuit,
wherein the customized profile associated with the anticipated patient is stored within a memory associated with the patient, and wherein the processor retrieves the customized profile associated with the anticipated patient from the memory associated with the anticipated patient via the input circuit, and determines that the patient is the anticipated patient based on receipt of the customized profile associated with the anticipated patient.

7. The external defibrillator of claim 6, wherein the memory associated with the anticipated patient is a removable medium for the external defibrillator.

8. The external defibrillator of claim 6, wherein the memory associated with the anticipated patient comprises a radio frequency identification (RFID) device that is interrogated by the external defibrillator.

9. The external defibrillator of claim 6, wherein the memory associated with the anticipated patient comprises a memory within a consumer electronic device of the anticipated patient.

10. The external defibrillator of claim 6, wherein the memory associated with the anticipated patient comprises a memory that is accessible by the external defibrillator via a network.

11. The external defibrillator of claim 1, wherein the profiles comprise defibrillation therapy parameters, and the processor controls delivery of defibrillation according to the defibrillation therapy parameters of one of the profiles.

12. The external defibrillator of claim 1,
further comprising a patient interface circuit,
wherein the customized profile for the anticipated patient comprises a previous recording of a physiological parameter of the anticipated patient, and
wherein the processor acquires a current recording of the physiological parameter via the patient interface circuit, compares the current recording to the previous recording, and delivers therapy to the patient based on the comparison.

13. The external defibrillator of claim 1, wherein the processor updates the customized profile for the anticipated patient based on delivery of therapy to the anticipated patient.

14. The external defibrillator of claim 1, wherein if the processor determines that the patient is not the anticipated patient, the processor determines whether or not the patient is a child, selects one of a general adult profile or a general child profile based on the determination, and controls delivery of therapy according to the selected general profile.

15. The external defibrillator of claim 1, further comprising a user interface, wherein the processor provides prompts to the anticipated patient via the user interface based on the customized profile associated with the anticipated patient.

16. The external defibrillator of claim 1, further comprising a memory that stores the customized profile associated with the anticipated patient.

17. The external defibrillator of claim 1, further comprising a memory that stores the general profile.

18. The external defibrillator of claim 1, wherein the external defibrillator comprises an automated external defibrillator (AED).

19. A non-transitory computer-readable medium comprising instructions that cause a programmable processor to:
determine whether a patient is one of an anticipated patient or a non-anticipated patient, wherein the anticipated patient is an individual patient associated with a patient-specific, customized profile; and
control delivery of therapy to the patient via an external defibrillator according to one of a general profile if the patient is the non-anticipated patient or the customized profile if the patient is the anticipated patient.

20. The medium of claim 19, wherein the instructions that cause the processor to determine whether a patient is an anticipated patient comprise instructions that cause the processor to receive an indication from a user via a user interface of the external defibrillator.

21. The medium of claim 19, wherein the instructions that cause the processor to determine whether a patient is an anticipated patient comprise instructions that cause the processor to receive an indication from a patient identification device associated with the anticipated patient.

22. The medium of claim 19, further comprising instructions that cause the processor to:
receive information identifying the patient; and
select one of a plurality of patient-specific, customized profiles based on the identification,
wherein each of the patient-specific, customized profiles is associated with a respective one of a plurality of anticipated patients, and the instructions that cause the processor to control delivery of therapy comprise instructions that cause the processor to control delivery of therapy according to the selected customized profile.

23. The medium of claim 19,
wherein the customized profile associated with the anticipated patient is stored within a memory associated with the patient, the medium further comprising instructions that cause the processor to retrieve the customized profile associated with the anticipated patient from the memory associated with the anticipated patient, and
wherein the instructions that cause the processor to determine whether a patient is an anticipated patient comprise instructions that cause the processor to determine that the patient is the anticipated patient based on receipt by the external defibrillator of the customized profile associated with the anticipated patient from the memory associated with the anticipated patient.

24. The medium of claim 19, wherein the profiles comprise defibrillation therapy parameters, and the instructions that cause the processor to control delivery of therapy comprise instructions that cause the processor to control delivery of defibrillation therapy to the patient based on the parameters of one of the profiles.

25. The medium of claim 19, wherein the customized profile for the anticipated patient comprises a previous recording of a physiological parameter of the anticipated patient, and the instructions that cause the processor to control delivery of therapy to the patient comprise instructions that cause the processor to:
acquire a current recording of the physiological parameter via the external defibrillator;
compare the current recording to the previous recording; and
deliver therapy based on the comparison.

26. The medium of claim 19, further comprising instructions that cause the processor to update the customized profile associated with the anticipated patient based on the delivery of therapy to the anticipated patient.

27. The medium of claim 19, further comprising instructions that cause the processor to:
determine that the patient is not the anticipated patient;
determine whether the patient is a child; and
select one of a general adult profile or a general child profile based on the determination,
wherein the instructions that cause a processor to control delivery of therapy comprise instructions that cause the processor to control delivery of therapy according to the selected general profile.

* * * * *

UNITED STATES PATENT AND TRADEMARK OFFICE
CERTIFICATE OF CORRECTION

| | | |
|---|---|---|
| PATENT NO. | : 7,805,190 B2 | Page 1 of 1 |
| APPLICATION NO. | : 10/810045 | |
| DATED | : September 28, 2010 | |
| INVENTOR(S) | : Chapman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1321 days.

Signed and Sealed this
Seventeenth Day of May, 2011

David J. Kappos
*Director of the United States Patent and Trademark Office*